United States Patent [19]

Pinkos et al.

[11] Patent Number: 5,646,307
[45] Date of Patent: Jul. 8, 1997

[54] PREPARATION OF γ-BUTYROLACTONE

[75] Inventors: Rolf Pinkos, Bad Dürkheim; Rolf Fischer, Heidelberg, both of Germany

[73] Assignee: BASF Aktiengesellschaft, Ludwigshafen, Germany

[21] Appl. No.: 640,879

[22] PCT Filed: Nov. 9, 1994

[86] PCT No.: PCT/EP94/03683

§ 371 Date: May 16, 1996

§ 102(e) Date: May 16, 1996

[87] PCT Pub. No.: WO95/14010

PCT Pub. Date: May 26, 1995

[30] Foreign Application Priority Data

Nov. 18, 1993 [DE] Germany .......... 43 39 269.5

[51] Int. Cl.$^6$ .......... C07D 307/02
[52] U.S. Cl. .......... 549/295
[58] Field of Search .......... 549/295

[56] References Cited

U.S. PATENT DOCUMENTS 5,034,545 7/1991 Fischer .......... 549/507
5,082,956 1/1992 Monnier et al. .......... 549/507

FOREIGN PATENT DOCUMENTS 024 770 3/1981 European Pat. Off. .

OTHER PUBLICATIONS

Methoden der Org. Chem., vol. V, 1c, pp. 16–26 (1980).
J. Mol. Cat., 72 (1992) 143–152.
Tetrahedron Lett. 39, (1977) pp. 3483–3484.
J. Or. Chem., vol. 41, No. 3, 1976 p. 513.
Bull. Soc. Chem., France 668 (1950).
J.C.S. Perkin II, J. Chem. Soc. II 366, (1972).

*Primary Examiner*—Amelia Owens
*Attorney, Agent, or Firm*—Keil & Weinkauf

[57] ABSTRACT

A process for the preparation of γ-butyrolactone, in which 2,5-dihydrofuran or 2,3-dihydrofuran or a mixture of these two dihydrofurans is caused to react in the gas phase in the presence of water and in the presence or absence of additional hydrogen at elevated temperature over a hydrogenating catalyst.

10 Claims, No Drawings

PREPARATION OF γ-BUTYROLACTONE

The present invention relates to a process for the preparation of γ-butyrolactone.

Havel et al (*J. Org. Chem.* 41, 513 (1976)) produced γ-butyrolactone by oxidation of 2,3-dihydrofuran with triplet oxygen. γ-butyrolactone forms in this reaction only in a yield of 1.4%. Piancatelli et al (*Tetrahrahedron Lett.* 39, 3483 (1977)) oxidized 2,3-dihydrofuran by means of pyridinium chlorochromate. The expensive oxidizing agent pyridinium chlorochromate is consumed in this reaction in stoichiometric amounts, for which reason this process is unsuitable, since it is uneconomical for commercial use.

It has not hitherto been possible to obtain γ-butyrolactone starting from 2,5-dihydrofuran by a direct method. Alper et al (*J. Mol. Cat.* 72, 143 (1992)) described the cobalt(I) chloride-catalyzed oxidation of 2,5-dihydrofuran with oxygen to form 2-buten-4-olide of the formula I

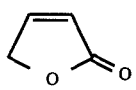
I whose C—C double bond has to be hydrogenated in a subsequent reaction before γ-butyrolactone is obtained. Thus this process is also uneconomical.

According to EP-A 24,770, the reaction of 2,5-dihydrofuran in the liquid phase with water over a platinum/palladium-on-aluminum oxide catalyst leads to 4-hydroxybutyraldehyde. γ-Butyrolactone was not found in this reaction.

γ-Butyrolactone is a chemical required in large quantities and serves, for example, as solvent for polyacrylonitrile, cellulose acetate, polystyrene, shellac, and resins and is also used as starting material for the preparation of economically important products such as pyrrolidone, N-methyl pyrrolidone and poly(vinyl pyrrolidone).

It was the object of the present invention to provide a process which makes possible the preparation of γ-butyrolactone, starting from 2,5-dihydrofuran or 2,3-dihydrofuran, in an economical manner. In particular it was desirable to find a way to prepare γ-butyrolactone starting from 2,5-dihydrofuran directly in a single stage.

Accordingly we have found a process for the preparation of γ-butyrolactone, which is characterized in that 2,5-dihydrofuran or 2,3-dihydrofuran or a mixture of these two dihydrofurans is caused to react in the gas phase in the presence of water and in the presence or absence of additional hydrogen at elevated temperature over a hydrogenating catalyst.

Although the chemical reaction mechanism for the reaction underlying the process according to the invention is still unknown, it is thought that this reaction could occur according to the following reaction scheme. If this is so, the 2,5-dihydrofuran II is initially isomerized over the hydrogenating catalyst according to equation (1) to form 2,3-dihydrofuran III:

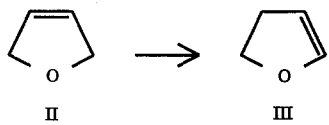

Then water is possibly added to the 2,3-dihydrofuran according to equation (2):

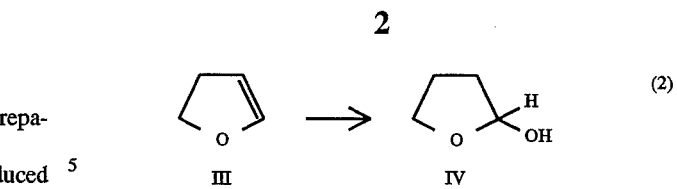

in which 2-hydroxytetrahydrofuran of the formula IV forms, which is in a balanced relationship with its open-chain isomer 4-hydroxybutyraldehyde of the formula V

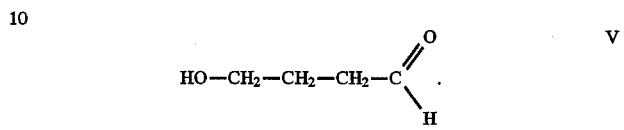

2-Hydroxytetrahydrofuran IV is then presumably hydrogenated by the hydrogenation catalyst according to equation (3)

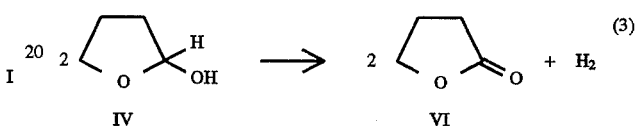

to form γ-butyrolactone of the formula VI. The hydrogenation catalyst employed would thus act as a dehydrogenation catalyst. Since the catalysts which can be used in the invention are usually employed as hydrogenation catalysts in industry, we will continue to call these catalysts "hydrogenation catalysts" for the purposes of this application in spite of their dehydrogenating effect in the process according to the invention. As mentioned above, the above reaction mechanism is merely an attempt at an explanation of the chemical events taking place at the catalyst in the process according to the invention, which have not been investigated in greater detail. This idea concerning the reaction mechanism is substantially supported by the observations that both 2,5-dihydrofuran and 2,3-dihydrofuran can be employed in the process of the invention and that the said process can be carried out in the absence of additional hydrogen, and is also supported by the by-products found.

In the process according to the invention 2,5-dihydrofuran or 2,3-dihydrofuran or a mixture of these compounds, preferably 2,5-dihydrofuran alone, is caused to react in the gas phase with water in a molar ratio of dihydrofuran to water of in general from 2:1 to 1:100, preferably from 1:1 to 1:50 and more preferably from 1:1 to 1:10 in the presence of a hydrogenating catalyst under a pressure of in general from 0.5 to 50 bar, preferably from 0.8 to 40 bar and in particular from 1 to 10 bar, at a temperature of from 100° to 350° C., preferably from 130° to 330° C. and more preferably from 170° to 300° C., to produce γ-butyrolactone.

Suitable hydrogenation catalysts for use in the process of the invention are virtually all heterogeneous catalysts suitable for the hydrogenation of carbonyl groups, for example, those described in Houben-Weyl, *Methoden der Organischen Chemie*, Vol. V, 1c, pp 16–26 Thieme-Verlag Stuttgart, 1980. In the process according to the invention, the hydrogenation catalysts can be disposed in a fixed bed or be mobile, eg, located in a fluid bed in the reactor.

It is preferred to use, in the process according to the invention, those heterogeneous hydrogenation catalysts which contain one or more elements of Groups Ib, VIb, VIIb and VIIIb of the Periodic Table. These catalysts can furthermore contain, to promote their catalytical activity and selectivity, additionally one or more elements selected from Groups Ia, IIa, IIIa, IVa, and Va of the Periodic Table. Preferred catalysts are in particular those which contain, as catalytically active components, eg, copper, chromium, rhenium, cobalt, nickel, rhodium, ruthenium, iridium, palladium, iron, or platinum or mixtures of a number of these elements as well as, optionally, additional components capable of influencing their catalytical activity and selectivity, eg, indium, tin, or antimony. Particularly preferred hydrogenation catalysts used in the process according to the invention are those which contain rhenium and/or copper.

The heterogeneous catalysts which can be employed in the process according to the invention are either so-called precipitation catalysts or conventional supported catalysts which have been prepared by applying the catalytically active component to a support material.

The precipitation catalysts can be prepared by precipitating their catalytically active components from their salt solutions, in particular from the solutions of their nitrates and/or acetates, by the addition of solutions of alkali metal and/or alkaline earth metal hydroxides and/or carbonates, eg, as difficultly soluble hydroxides, oxide hydrates, basic salts, or carbonates, then drying the precipitate obtained and subsequently converting it by calcination at in general from 300° to 700° C., in particular from 400° to 600° C., to the corresponding oxides, mixed oxides and/or oxides of mixed-valency, which are reduced by treatment with hydrogen or gases containing hydrogen at usually from 50° to 700° C., in particular at from 100° to 400° C. to the respective metals and/or oxidic compounds of lower oxidation stage and are converted to their catalytically active form. Instead of hydrogen, other suitable reducing agents, eg, hydrazine can be used for this purpose, if desired. However the use of hydrogen is preferred. During this process, reduction is usually continued until virtually no more hydrogen is consumed. In the preparation of precipitation catalysts containing a support material, the precipitation of the catalytically active components can take place in the presence of the respective support material. However, the catalytically active components may advantageously be precipitated simultaneously with the support material from the respective salt solutions. Suitable support materials are, eg, the oxides of aluminum and titanium, zinc oxide, zirconium dioxide, silicon dioxide, argillaceous earths, eg, montmorrillonites, silicates, such as magnesium silicates or aluminum silicates or zeolites, such as zeolites ZSM 5 or ZSM 10. Mixtures of such support materials can also be used. The dried precipitate coming from the precipitation stage may, if desired, be admixed, prior to calcination, with molding aids such as graphite, talcum, or stearin, and/or with expanding agents such as cellulose, methyl cellulose, starch, wax, paraffin, and/or a poly(alkylene glycol), and compressed or extruded to shaped catalyst units such as pellets, balls, rings, or extrudates.

It is preferred to use, in the process according to the invention, hydrogenation catalysts which contain the metals or metal compounds which catalyze the hydrogenation deposited on a support material. Apart from the aforementioned precipitation catalysts which contain a support material in addition to the catalytically active components, in general those supported catalysts are particularly well suited for use in the process according to the invention in which the catalytically active components have been applied to a support material, eg, by impregnation.

The way in which the catalytically active metals are applied to the support is not usually important and this can be brought about in a variety of ways. The catalytically active metals can be applied to these support materials, eg, by impregnation with solutions or suspensions of the salts or oxides of the elements concerned, and drying followed by reduction of the metal compounds to the respective metals or compounds of lower oxidation stage by means of a reducing agent, for example, hydrogen, gases containing hydrogen, or hydrazine, preferably with gases containing hydrogen. The reduction of the metal compounds deposited on the support material can take place under the same conditions as described above for the precipitation catalysts. Another possibility for the application of the catalytically active metals to these supports consists in impregnating the supports with solutions of thermally readily decomposable salts, eg, nitrates or thermally readily decomposable complex compounds, eg, carbonyl or hydride complexes of the catalytically active metals, and heating the thus impregnated support to achieve thermal decomposition of the adsorbed metal compounds, at temperatures of from 300° to 600° C. This thermal decomposition is preferably effected under a blanket of protective gas. Suitable protective gases are, eg, nitrogen, carbon dioxide, hydrogen, or the noble gases. Furthermore, the catalytically active metals can be deposited on to the catalyst support by vapor deposition or flame spraying. In this case metal wire gauzes or metal foils may also serve as support materials.

The content of the catalytically active metals in the supported catalysts is not critically important, theoretically, for the success of the process according to the invention. The person skilled in the art will of course realize that higher contents of catalytically active metals in these supported catalysts can lead to higher space-time conversions than lower contents. In general, supported catalysts are used whose content of catalytically active metals is from 0.1 to 90 wt %, preferably from 0.5 to 40 wt %, based on the total catalyst. Since these content data refer to the total catalyst including support material, and since the different support materials have, however, greatly differing specific weights and specific surface areas, the above values can be deviated from, above or below, without this having a negative effect on the results of the process according to the invention. There can, of course, be applied a number of catalytically active metals to the respective support material. Furthermore, the catalytically active metals can be applied to the support, for example, by the process described in DE-A 2,519,817, EP-A 147,219, and EP-A 285,420. In the catalysts described in to the aforementioned references the catalytically active metals are present as alloys, which are produced by thermal treatment and/or reduction of the salts or complexes of the metals cited above, which have been deposited on a support, eg, by impregnation.

The support materials used are, in general, the oxides of aluminum and titanium, zinc oxide, zirconium dioxide, silicon dioxide, argillaceous earths, eg, montmorillonites, silicates, such as magnesium silicates or aluminum silicates, zeolites, such as zeolites ZSM 5 or ZSM 10, as well as activated charcoal. Preferred support materials are aluminum oxides, titanium dioxides, silicon dioxide, zirconium dioxide, or activated charcoal. It is also possible, of course, to use mixtures of different support materials as supports for the hydrogenation catalysts which can be employed in the process according to the invention.

Examples of hydrogenation catalysts suitable for use in the process according to the invention are the following:

Platinum on activated charcoal, palladium on activated charcoal, palladium on aluminum oxide, cobalt on activated charcoal, cobalt on silicon dioxide, cobalt on aluminum oxide, iron on activated charcoal, manganese on activated charcoal, rhenium on activated charcoal, rhenium on silicon dioxide, rhenium/tin on activated charcoal, rhenium/ palladium on activated charcoal, copper on activated charcoal, copper on silicon dioxide, copper on aluminum oxide, copper chromite, as well as the catalysts described in DE-A 392,332, U.S. Pat. No. 3,449,445, EP-A 44,444, EP-A 147,219, DE-A 3,904,083, DE-A 2,321,101, ET-A 415,202, DE-A 2,366,264, and EP-A 100,406.

Particularly preferred catalysts contain at least one of the metals copper and rhenium. Copper-containing precipitation catalysts can contain in general from 0.1 to 90 wt %, preferably from 1 to 80 wt % and more preferably from 5 to 50 wt % of copper, calculated as CuO and based on the total weight of the catalyst. Copper-containing supported catalysts, prepared by impregnation or coating of a support material, can contain in general from 0.1 to 30 wt %, preferably from 1 to 30 wt % and more preferably from 3 to 25 wt % of copper, calculated as CuO and based on the total weight of the catalyst. Rhenium-containing catalysts are employed in the process according to the invention preferably in the form of supported catalysts, which contain rhenium, calculated as Re and based on the total weight of the catalyst, in amounts of from 0.1 to 25 wt %, preferably from 1 to 20 wt % and more preferably from 2 to 10 wt %.

The process according to the invention is advantageously carried out continuously. In this process use can be made, for example, of tubular reactors, in which the catalyst is advantageously arranged in the form of a fixed bed, or fluidized bed reactors, in which the catalyst is agitated by a stream of gas.

The educts 2,5-dihydrofuran and/or 2,3-dihydrofuran and water can be transformed to the gas phase, eg, in an evaporator, before they are passed over the catalyst. The educts are advantageously vaporized in a stream of carrier gas, there being employed, as carrier gases, for example, noble gases, nitrogen, $C_1$–$C_4$ hydrocarbons, preferably methane, and preferably hydrogen. The stream of carrier gas is metered in such a manner that the educts, products, and any by-products formed, eg, 1,4-butanediol, tetrahydrofuran, and butanol, remain gaseous in the reactor during the process.

If desired, the stream of carrier gas serving for vaporization of the educts can, advantageously, be recycled, ie it can be re-used as stream of carrier gas for vaporization of the educts following deposition of the products contained therein on leaving the catalyst bed, for example, in a gas/liquid separator or condenser. If no recycling of the gas is employed or a carrier gas other than hydrogen is used, the hydrogen liberated at the catalyst during the reaction according to equation (3) suffices to keep the hydrogenating catalyst active.

In general, the specific throughput, per unit catalyst, in the process according to the invention is from 0.05 to 5 kg of dihydrofuran per liter of catalyst per hour, preferably from 0.1 to 3 kg of dihydrofuran per liter of catalyst per hour.

The gaseous effluent can be worked up by distillation after cooling and condensation of the products, in conventional manner, for example, by fractional distillation. It is also possible to pass the gaseous effluent directly to a distillation column. During said distillation, there can be isolated, apart from the end product γ-butyrolactone, any by-products contained in the effluent, such as 1,4-butanediol, tetrahydrofuran and/or n-butanol, as desirable products. Any 2,5- and/or 2,3-dihydrofuran and/or water contained in the effluent can be separated during distillation of the product and, after vaporization, be recycled to the reactor.

The process according to the invention thus makes it possible to prepare γ-butyrolactone in an economical manner starting from 2,5-dihydrofuran and/or 2,3-dihydrofuran.

It is particularly advantageous that γ-butyrolactone can be produced from 2,5-dihydrofuran by this process in a single stage.

The starting material used in the invention, 2,5-dihydrofuran, can be prepared by isomerization of vinyl oxirane, for example, by the process described in U.S. Pat. No. 5,034,545 und U.S. Pat. No. 5,082,956. 2,3-Dihydrofuran can be obtained from 2,5-dihydrofuran by base-catalyzed or photochemically catalyzed isomerization therof, for example, by the process described by Paul et al (*Bull. Soc. Chim. France* 668 (1950)) or Hubert et al (*J. Chem. Soc.* Perkin I 366 (1972)).

EXAMPLES

The selectivities stated in the following examples (yield/conversion×100) were determined by gas chomatographic methods using an internal standard.

Example 1

In a gas phase reactor having a capacity of 160 mL and equipped with external heating means there were placed, in the form of gravel, 102 g of a copper on silicon dioxide catalyst (copper content: 22 wt %, calculated as Cuo and based on the total weight of the catalyst; prepared by impregnation of the support with an ammoniacal copper carbonate solution, drying of the impregnated support at 120° C. and calcination at 500° C.) and reduced in a stream of hydrogen at a temperature rising from initially 150° C. to a final temperature of 250° C. Thereafter 33 mL/h of water and 16 mL/h of 2,5-dihydrofuran were continuously vaporized at 200° C./1013 mbar in a pre-evaporator in a stream of hydrogen flowing at a rate of 18 L/h and passed to the reactor having a temperature of 210° C. The effluent was collected in a cooled receiver and analyzed. At a conversion of 58%, γ-butyrolactone was obtain with a selectivity of 83% (2,3-dihydrofuran: 0.4%; furan: 4%; tetrahydrofuran: 9%; n-butanol: 3%; remainder: small amounts of various low-boiling fractions, such as propanol, which were not analyzed).

Example 2

In a manner similar to that described in Example 1 15 mL/h of 2,5-dihydrofuran and 32 mL/h of water were passed at 220° C. over 149 g of a catalyst containing copper and magnesium on silicon dioxide (composition: copper, calculated as Cuo: 43.0 wt %; magnesium, calculated as MgO: 18.0 wt %; silicate, calculated as $SiO_2$: 35.0 wt %; barium, calculated as BaO: 1 wt %; chromium, calculated as $Cr_2O_3$: 0.6 wt %; zinc, calculated as ZnO: 0.4 wt %; sodium, calculated as $Na_2O$: 0.2 wt %; the remainder being predominantly carbonate; all data based on the total weight of the catalyst; prepared by concurrent precipitation from a solution of the metal salts and sodium silicate (waterglass) with sodium carbonate, drying of the precipitate, extrusion to extrudates using talcum as molding auxiliary and calcination at 500° C., and reduction in a manner similar to that described in Example 1). At a conversion of 97%, γ-butyrolactone was obtained with a selectivity of 85% (2,3-dihydrofuran: 1.4%; furan: 3%; tetrahydrofuran: 9%; n-butanol: 1%; remainder: small amounts of various non-analyzed low-boiling fractions).

Example 3

In a manner similar to that described in Example 1, 19 mL/h of 2,5-dihydrofuran and 11 mL/h of water were passed over 142 g of the catalyst described in Example 2. At a conversion of 99.7% γ-butyrolactone was obtained with a selectivity of 89% (2,3-dihydrofuran: 0.13%; furan: 3.9%; tetrahydrofuran: 5%; n-butanol: 1.7%; remainder: small amounts of various non-analyzed low-boiling fractions).

Example 4

In a manner similar to that described in Example 1, 8 mL/h of 2,5-dihydrofuran and 15 mL/h of water were passed at 210° C. over 85 g of a copper-on-activated charcoal catalyst (copper content: 10 wt %, calculated as CuO and based on the total weight of the catalyst; prepared by impregnation of 4 mm activated charcoal extrudates using an ammoniacal copper carbonate solution; drying at 120° C. and reduction in a manner similar to that described in Example 1). At a conversion of 98%, γ-butyrolactone was formed with a selectivity of 83% (2,3-dihydrofuran: 2%; furan: 4%; tetrahydrofuran: 4%; n-butanol: 1%; 4-hydroxybutyraldehyde: 5%; 1,4-butanediol: 0.2%; remainder: small amounts of various non-analyzed low-boiling fractions).

Example 5

In a manner similar to that described in Example 1, 10 mL/h of 2,5-dihydrofuran and 9 mL/h of water were passed over 73 g of a rhenium-on-activated charcoal catalyst (rhenium content: 6 wt %, calculated as Re; prepared by impregnation of 4 mm activated charcoal extrudates with an aqueous dirhenium heptoxide $Re_2O_7$ solution; drying at 120° C.; reduction in a manner similar to that described in Example 1). At a conversion of 99%, γ-butyrolactone was formed with a selectivity of 91% (2,3-dihydrofuran: 0.5%; furan: 1%; tetrahydrofuran: 5%; n-butanol: 1%; remainder: small amounts of various non-analyzed low-boiling fractions).

Example 6

In a manner similar to that described in Example 5 14 mL/h of 2,5-dihydrofuran and 24 mL/h of water were passed over the rhenium-on-activated charcoal catalyst at 220° C. At quantitative conversion, γ-butyrolactone was formed with a selectivity of 87% (furan: 2.5%; tetrahydrofuran: 9%; n-butanol: 1%; remainder: various non-analyzed low-boiling fractions).

Example 7

In a manner similar to that described in Example 1, 16 mL/h of 2,5-dihydrofuran and 30 mL/h of water were passed at 230° C. over 253 g of the commercially available copper chromite catalyst marketed by Suedchemie, Munich and bearing the connotation G 22 (composition according to sales brochure: 37% of Cu; 46% of $Cr_2O_3$; 13% of BaO; reduction in a manner similar to that described in Example 1). At a conversion of 71%, γ-butyrolactone was formed with a selectivity of 67% (2,3-dihydrofuran: 8%; furan: 3%; tetrahydrofuran: 2%; n-butanol: 1%; 4-hydroxybutyraldehyde: 0.5%; remainder: various non-analyzed low-boiling fractions).

Example 8

In a manner similar to that described in Example 1 10 mL/h of 2,3-dihydrofuran and 8 mL/h of water were passed at 220° C. in a stream of carrier gas comprising 13 L/h of hydrogen over 47 g of the rhenium-on-activated charcoal catalyst described in Example 5 (reactor volume: 100 mL). At a conversion of 99.5%, γ-butyrolactone was formed with a selectivity of 98% (tetrahydrofuran: 0.3%; 4-hydroxybutyraldehyde: 0.5%; remainder: small amounts of various non-analyzed low-boiling fractions).

Example 9

In a manner similar to that described in Example 8, 10 mL/h of 2,3-dihydrofuran and 10 mL/h of water were passed at 220° C. in a stream of carrier gas comprising 13 L/h of hydrogen over 45 g of a rhenium/palladium-on-activated charcoal catalyst (rhenium content: 3 wt %, calculated as Re; palladium content: 3 wt %, calculated as Pd; in each case based on the total weight of the catalyst; prepared by impregnation of 4 mm activated charcoal extrudates with a solution of $PdCl_2$ in aqueous hydrochloric acid, drying and repeated impregnation of the support with an aqueous dirhenium heptoxide $Re_2O_7$ solution; drying at 120° C. and reduction as described in Example 1). At a conversion of 99.5%, γ-butyrolactone was formed with a selectivity of 1%.

After changing the stream of carrier gas from hydrogen to 12 L/h of nitrogen, γ-butyrolactone was obtain at quantitative conversion with a selectivity of 15%.

We claim:

1. A process for the preparation of γ-butyrolactone, wherein 2,5-dihydrofuran or 2,3-dihydrofuran or a mixture of these two dihydrofurans is caused to react in the gas phase in the presence of water and in the presence or absence of additional hydrogen at elevated temperature over a hydrogenating catalyst.

2. A process as defined in claim 1, wherein the reaction is carried out in the presence of additional hydrogen.

3. A process as defined in claim 1, wherein the reaction is carried out in the presence of additional hydrogen, the hydrogen serving as carrier gas.

4. A process as defined in claim 1, wherein the reaction is carried out at a temperature of from 100° to 350° C. and a pressure of from 0.5 to 50 bar.

5. A process as defined in claim 1, wherein a hydrogenating catalyst is used which contains at least one element selected from Groups Ib, VIb, VIIb and/or VIIIb of the Periodic Table.

6. A process as defined in claim 1, wherein a hydrogenating catalyst is used which contains apart from at least one element selected from the Groups Ib, VIb, VIIb and/or VIIIb in addition at least one element selected from the Groups IIb, Ia, IIa, IIIa, Va and/or VIa of the Periodic Table.

7. A process as defined in claim 1, wherein a hydrogenating catalyst is used which contains rhenium.

8. A process as defined in claim 1, wherein a hydrogenating catalyst is used which contains copper.

9. A process as defined in claim 1, wherein the hydrogenating catalyst used is a supported catalyst.

10. A process as defined in claim 1, wherein the hydrogenating catalyst is reduced, prior to commencement of the reaction, with hydrogen or a gas mixture containing hydrogen.

* * * * *